United States Patent
Lechmann et al.

(10) Patent No.: US 8,702,797 B2
(45) Date of Patent: Apr. 22, 2014

(54) INTERVERTEBRAL IMPLANT

(75) Inventors: Beat Lechmann, Grenchen (CH); Roger Buerki, Balsthal (CH); Mario Gago, Basel (CH); Robert Frigg, Bettlach (CH); Michael H. Mayer, Graefelfing (DE)

(73) Assignee: DePuy Synthes Products, LLC, Raynham, MA (US)

( * ) Notice: Subject to any disclaimer, the term of this patent is extended or adjusted under 35 U.S.C. 154(b) by 1649 days.

(21) Appl. No.: 11/839,088

(22) Filed: Aug. 15, 2007

(65) Prior Publication Data

US 2008/0033554 A1 Feb. 7, 2008

Related U.S. Application Data

(63) Continuation of application No. PCT/CH2005/000087, filed on Feb. 16, 2005.

(51) Int. Cl.
*A61F 2/44* (2006.01)
(52) U.S. Cl.
USPC ............. 623/17.14; 623/17.11; 606/912
(58) Field of Classification Search
USPC ............... 606/912; 623/17.11, 17.14
See application file for complete search history.

(56) References Cited

U.S. PATENT DOCUMENTS

| | | | | |
|---|---|---|---|---|
| 4,349,921 A | * | 9/1982 | Kuntz | 623/17.16 |
| 5,895,428 A | * | 4/1999 | Berry | 623/17.15 |
| 6,517,580 B1 | * | 2/2003 | Ramadan et al. | 623/17.15 |
| 6,770,095 B2 | * | 8/2004 | Grinberg et al. | 623/17.14 |
| 2001/0012966 A1 | | 8/2001 | Studer et al. | |
| 2004/0030391 A1 | | 2/2004 | Ferree | |
| 2006/0229725 A1 | | 10/2006 | Lechmann et al. | 623/17.11 |

FOREIGN PATENT DOCUMENTS

| | | | | |
|---|---|---|---|---|
| DE | 28 04 936 | | 8/1979 | |
| DE | 203 13 183 | | 10/2003 | |
| JP | 2001204751 A | | 7/2001 | |
| WO | WO 03/084449 | * | 10/2003 | A61F 2/44 |
| WO | WO 03084449 A1 | * | 10/2003 | A61F 2/44 |
| WO | WO 2004/034935 | | 4/2004 | |
| WO | 2005011539 A2 | | 2/2005 | |

OTHER PUBLICATIONS

International Search Report, dated Jan. 30, 2006, in International Patent Application No. PCT/CH2005/000087.
Japanese Patent Office: Notice of Reasons for Rejection and accompanying English translation, Nov. 6, 2009.

* cited by examiner

*Primary Examiner* — Kevin T Truong
*Assistant Examiner* — Christian Sevilla
(74) *Attorney, Agent, or Firm* — Meunier Carlin & Curfman, LLC

(57) ABSTRACT

The inventive intervertebral implant (1), in particular an artificial intervertebral disc comprises a central axis (2), a top part (3) and a lower part (4), wherein A) the top part (3) is provided with a top apposition surface (5) which rests on a base plate of a superimposed vertebral body, B) the lower part (4) is provided with a lower apposition surface (6) for resting on the covering plate of an underneath vertebral body, C) one part (3, 4) comprises a convex joint element (12) provided with a convex sliding surface (11) and the other part (3, 4) comprises a joint shell (13) provided with a complementary concave surface, D) the convex joint element (12) and the convex joint shell (13) form a joint (9) by means of which the two parts (3, 4) are rotatable with respect to each other around at least one axis of rotation and E) the intervertebral implant (1) is permeable to x-rays.

23 Claims, 3 Drawing Sheets

INTERVERTEBRAL IMPLANT

CROSS REFERENCE TO RELATED APPLICATIONS

This Application is a continuation application of International application Ser. No. PCT/CH2005/000087 filed on Feb. 16, 2005 for "INTERVERTEBRAL IMPLANT" which is hereby incorporated by reference herein.

BACKGROUND OF THE INVENTION

1. Field of Invention

The invention relates to an intervertebral implant, especially to an artificial intervertebral disk of the introductory portion of claim 1.

2. Description of Related Art

After a damaged, natural intervertebral disk or a damaged Nucleus pulposus of an intervertebral disk is removed, implants or prostheses are introduced at the present time into the intervertebral space between two adjacent vertebrae. The objective of implanting such implants is to bring about natural conditions once again as far as possible, that is, to restore, in particular, the original intervertebral disk height and, with that, the original distance between the two adjacent vertebrae. Furthermore, it shall be possible to carry out movements of the adjacent vertebrae relative to one another in a natural way as far as possible without hindrance. For this purpose, it is essential to maintain movement possibilities while bending forwards or backwards, that is, during flexion and extension of the vertebrae, as well as during a lateral bending of the vertebrae within the natural limits. The natural ligaments and muscles along the spinal column essentially are left intact, so that these further stabilize the movements of a mechanical replacement for an intervertebral disk.

Such an intervertebral implant is known from the DE 203 20 454 of MEISEL. This known implant comprises two cover plates, lying in contact with the bones, and a joint, which is disposed between the cover plates. This joint consists essentially of a spherically shaped first joint part and of a complementary joint shell as a second joint part, so that the cover plates can be swiveled polyaxially relative to one another. It is a disadvantage of this known intervertebral implant that it is opaque to x-rays and, accordingly, no longer permits adjacent vertebrae to be observed after an implantation.

SUMMARY OF THE INVENTION

The invention is to provide a remedy here. It is an object of the invention to provide an intervertebral implant, which is transparent to magnetic resonance imaging (MRI) as well as to x-rays, and accordingly permits post operative observation by means of x-rays and, at the same time, has a high MRI compatibility.

Pursuant to the invention, this objective is accomplished with an intervertebral implant, especially an artificial intervertebral disk, which has the distinguishing features of claim 1.

The advantages, which can be attained by the invention, are seen to lie essentially therein that, due to the inventive intervertebral implant, the MRI compatibility is increased and observation by means of x-rays becomes possible.

Further advantageous developments of the invention are characterized in the dependent claims.

In an example embodiment, each component of the invertebral implant comprises a radiolucent material. In another example embodiment, each component of the invertebral implant consists of a radiolucent material. In yet another example embodiment, the upper part and the lower part are made from a first x-ray-transparent material, whereas the convex part of the joint and the joint shell are made from a different, second, also x-ray-transparent material. In a further example, the upper portion and the lower portion are made from a first radiolucent material. In another example, the convex sliding portion and the concave sliding portion are made from a second radiolucent material. The advantages achieved thereby are to be seen essentially therein that sliding and abrasive wear properties, which are particularly advantageous for joint parts, can be used, whereas the outer parts can be produced from materials, which are suitable for contact with bones.

In a different embodiment, the individual parts of the intervertebral implant are made from the same material. The advantage of this embodiment lies therein that the elements, which come into contact with bones, can also be produced from ceramic materials.

In yet another embodiment, the x-ray-transparent material for the upper part and the lower part is selected from the group of poly(aryl ether) ketones, polyether ether ketones, ultrahigh molecular weight polyethylenes or polysulfones. In a further embodiment, the upper portion and the lower portion are made from a first radiolucent material, the first radiolucent material selected from the group of poly(aryl ether) ketones, polyether ether ketones, ultrahigh molecular weight polyethylenes or polysulfones.

In a further embodiment, the convex part of the joint and the joint shell are made from a ceramic material. In another embodiment, the convex sliding portion and the concave sliding portion are made from a ceramic material. The essential advantages of this embodiment are to be seen therein that the joint parts, made from ceramic materials, similar to cobalt chromiummolybdenum alloys, exhibit little abrasive wear during articulation movements, yet are transparent to MRI and x-rays.

In yet a further embodiment, the upper and lower apposition surfaces have a different shape from one another. The advantages, attainable thereby, lie particularly in producing a shape of the implant, which is advantageous with respect to the anatomy of the end plates. The intervertebral implants with different contact surfaces are suitable, above all, for the cervical vertebral column.

In a different embodiment, the upper and lower apposition surfaces have the same shape. Here, the advantages lie therein that the intervertebral implants with contact surfaces, symmetrical in the sagittal profile, are suitable, above all, for the lumbar vertebral column.

In once again a different embodiment, the convex part of the joint is connected firmly with one of the two parts and the joint shell is connected firmly with the other of the two parts. With that, the advantage can be achieved that the implant can be assembled before the implantation, so that a simpler insertion into the intervertebral space can also be attained.

In a further embodiment, the upper part and the lower part are provided with macroscopic structures at their apposition surfaces, so that migrational movements of the implanted intervertebral implant can be prevented.

In yet a further embodiment, connecting means are provided, by means of which the upper part and the lower part are held together without affecting the pivotability of the joint. The advantage of these connecting means lies therein that the intervertebral implant can be held together in situ and the parts cannot be lost.

In a different embodiment, the connecting means allow for an axial clearance of X>0 between the convex part of the joint and the joint shell during each articulation, so that a lubricating film of endogenous liquids can build up between the sliding surfaces.

In yet a different embodiment, the clearance X is at least 0.005 mm and preferably at least 0.05 mm.

In a further embodiment, the clearance X is not more than 0.5 mm and preferably not more than 0.6 mm.

In yet another embodiment, the connecting means comprise one anchoring element, which can be connected with one of the two parts and is supported loosely in the other of the two parts.

In a different embodiment, the convex part of the joint is a cavity, which is open at the apex of the convex part of the joint, lying on the central axis, and wherein the anchoring element can be moved axially so far, that, after overcoming the clearance X, it comes to lie axially in contact with the wall of the cavity.

In yet another embodiment, the components of the intervertebral implant consist of an x-ray-transparent material.

The invention and further developments of the invention are described in even greater detail in the following by means of partly diagrammatic representations of an example, of which

DETAILED DESCRIPTION OF THE CERTAIN EMBODIMENTS

Figure 1:
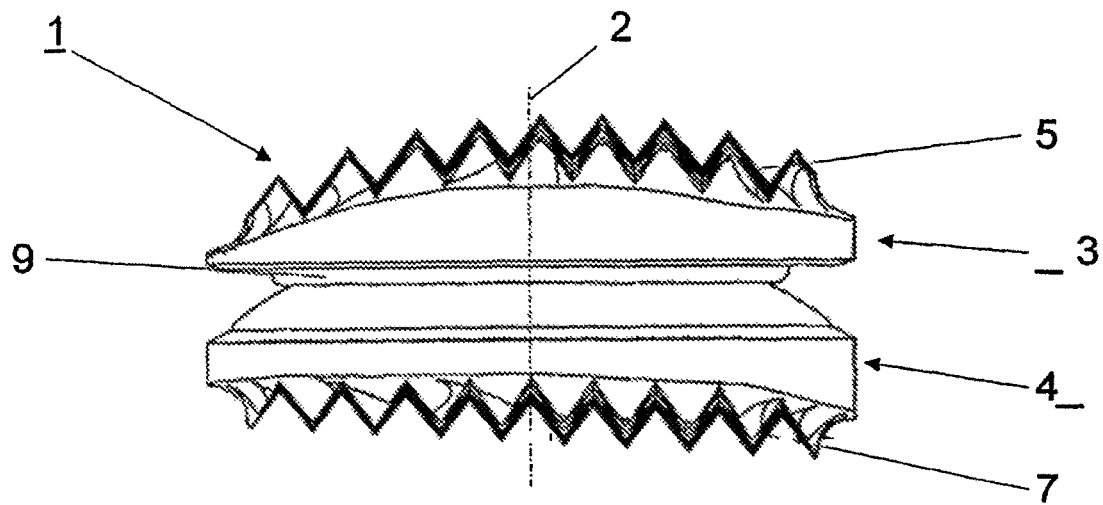
FIG. 1 shows a lateral view of an embodiment of the inventive intervertebral implant.

The embodiment of the inventive intervertebral implant 1, shown in FIGS. 1 and 2, comprises essentially an upper part 3 with an upper apposition surface 5 for contacting the base plate of the upper adjoining vertebral body and, intersecting the central axis 2, a lower part 4 with a lower apposition surface 7 for contacting the cover plate of the vertebra adjoining below and a joint 9, which is disposed between the two parts 3; 4 for the articulated connection between the two parts 3; 4. The joint 9 is constructed in two parts, the convex part 12 of the joint being constructed spherically in such a manner, that the central axis 2 intersects the apex vertically. At the rear end 16, which is the rear end of the convex part 12, the cross section of the convex part 12 of the joint, orthogonal to the central axis 2, is tapered and pressed or cast into a coaxial depression 17 in the lower part 4, which is complementary with the central axis 2. Analogously, the joint shell 13, which is constructed complementarily to the convex part 12 of the joint, is tapered at its rear end 21 in its cross section, which is orthogonal to the central axis 2, and pressed into a complementary depression 22 in the upper part 3. The upper and lower parts 3; 4, as well as the joint shell 13 and the convex part 12 of the joint, are constructed as separate pieces, so that the upper and lower parts 3; 4 can be produced, for example from PEEK, whereas the convex part 12 of the joint and the joint shell 13 can be produced, for example, from a ceramic material. The convex sliding surface 11 at the convex part 12 of the joint and the concave sliding surface 10 at the joint shell 13 have the same radius. This permits the convex part 12 of the joint and the joint shell 13 to slide relative to one another.

Furthermore, the upper and lower apposition surfaces 5; 7 have different shapes. The lower apposition surface 7 is constructed concavely, whereas the upper apposition surface 5 is constructed convexly.

Figure 2:
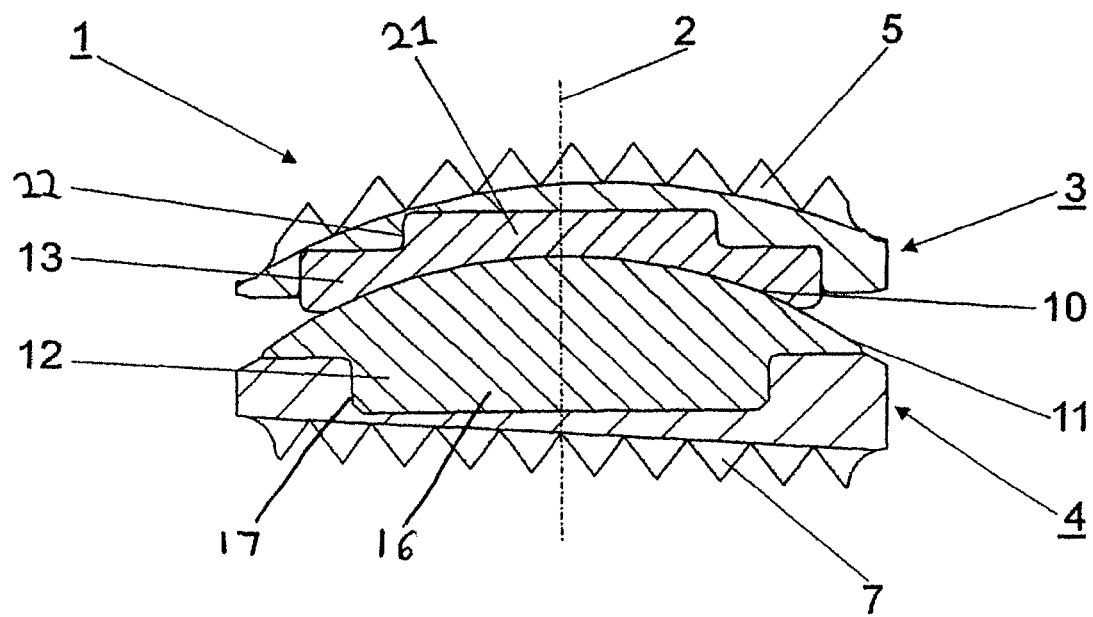
FIG. 2 shows a section through the embodiment of the inventive intervertebral implant, shown in FIG. 1.
Figure 3:
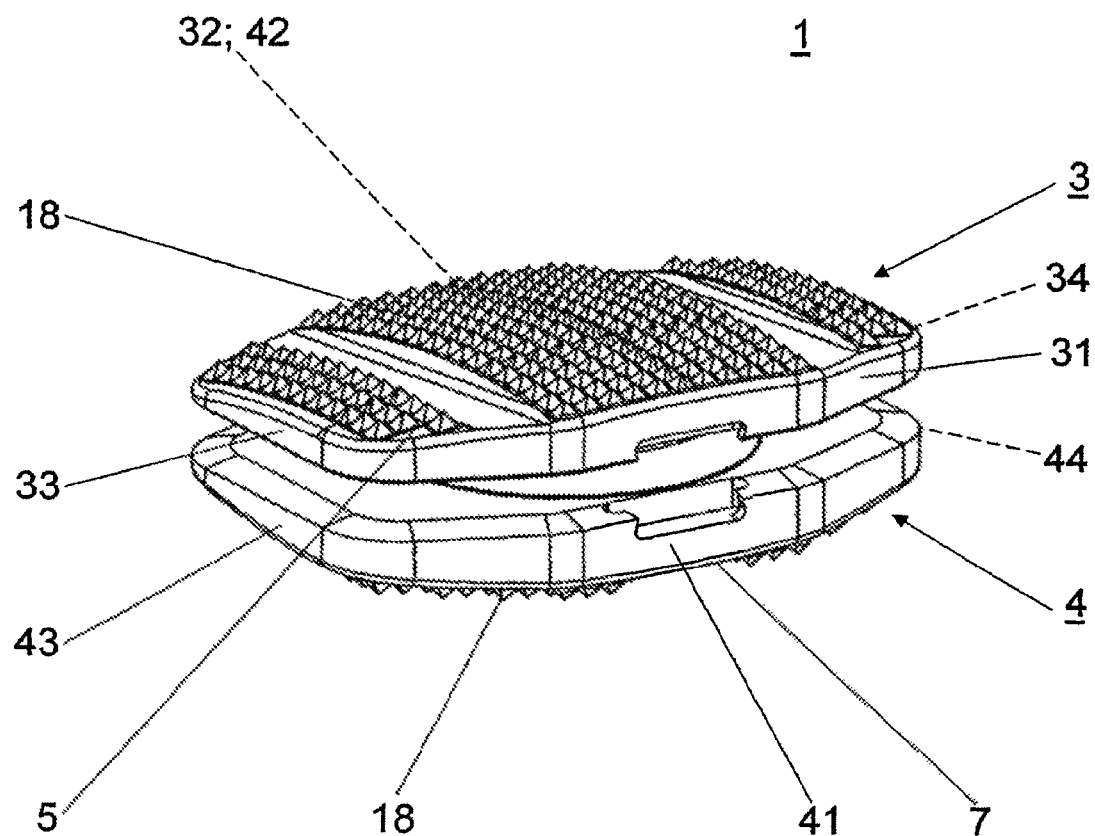
FIG. 3 shows a perspective view of a further embodiment of the inventive intervertebral implant.
Figure 4:
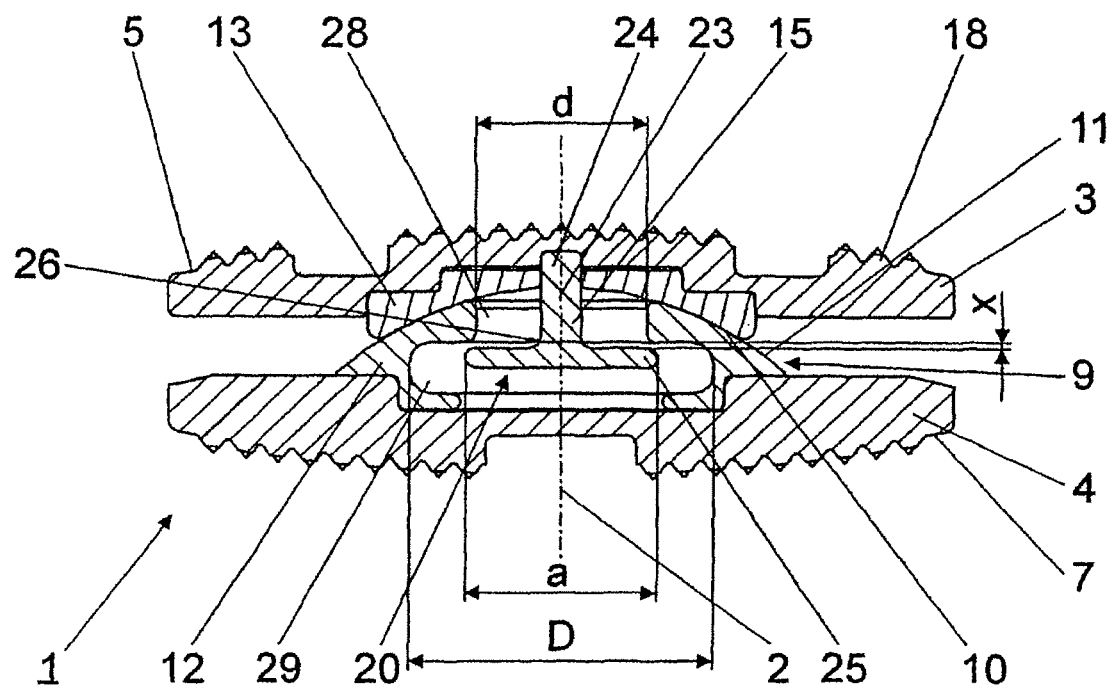
FIG. 4 shows a longitudinal section through the embodiment of the inventive, intervertebral implant, shown in FIG. 3.

The embodiment, shown in FIGS. 3 and 4, differs from that shown in FIGS. 1 and 2 firstly therein that it has two convex apposition surfaces 5; 7. The two parts 3; 4 each have a ventral side surface 31; 41, each have a dorsal side surface 32; 42 and each have two lateral side surfaces 33; 34; 43; 44 and macroscopic structures 18 on the apposition surfaces 5; 7. Secondly, the joint 9 is held together axially with the upper and the lower parts 3; 4 by means of connecting means 20 (FIG. 4). The connecting means 20 comprise an anchoring element 15, which is disposed coaxially with the central axis 2, and a pin 23, the rear end 24 of which passes through the joint shell 13 at the apex and is fastened at the upper part 3. Furthermore, the anchoring element 15 comprises a disk-shaped expansion 25, which has a larger diameter and is disposed at the front end 26 of the pin 23. The concave part 12 of the joint has an opening 28, which is coaxial with the central axis 2 and ends in a cylindrical cavity 29 in the interior of the convex part 12 of the joint, the cylindrical cavity 29 having a larger diameter. The geometry of the anchoring element 15, as well as of the opening 28 and of the cavity 29, is selected so that the pin 23 is disposed movably in the opening 28 and in the expansion 25 in the cavity 29. The diameter "d" of the opening 28 is smaller than the diameter "a" of the circular disc-shaped expansion 25, whereas the diameter "D" of the cavity 29 is larger than the diameter "a", so that the convex part 12 of the joint and the joint shell 13 and, with that, the two parts 3; 4, attached thereto, are held together axially without interference with the movement of the joint 9. The mobility of the pin 23 in the opening 28 and the expansion 25 in the cavity 29 enable the two parts 3; 4 to be swiveled polyaxially relative to one another. The length of the pin 23 is such that the expansion 25 comes into contact with the front end 26 of the pin 12 during each articulation of the joint 9 only after the clearance X at the transition between an opening 28 and the cavity 29 has been overcome.

We claim:

1. An intervertebral implant, comprising:
an upper portion that is made from a first x-ray transparent material and comprises:
a first part having an upper apposition surface to contact a base plate of a vertebra lying above the upper apposition surface, and
a separate second part having a concave sliding portion, the second part coupled to the first part;
a lower portion that is made from the first x-ray transparent material and comprises:
a first part having a lower apposition surface to contact a cover plate of a vertebra lying below the lower apposition surface, and
a separate second part having a convex sliding portion;
wherein the convex sliding portion and the concave sliding portion form a joint through which the upper portion and the lower portion are rotatable relative to each other,
wherein the second part of the upper portion is permanently coupled with the first part of the upper portion and the second part of the lower portion permanently coupled with the first part of the lower portion,
wherein the upper portion is permanently connected with the lower portion at a pin movably coupled with the lower portion and fixedly connected with the upper portion such that the pin extends through the second part of the upper portion and is fixedly connected to the first part of the upper portion; and wherein the second part of the upper portion including the concave sliding portion is made from a second x-ray transparent material that is different from the first x-ray transparent material.

2. The intervertebral implant of claim 1, wherein the convex sliding portion is made from the second x-ray transparent material.

3. The intervertebral implant of claim 1, wherein the first x-ray transparent material is selected from the group of poly (aryl ether) ketones, polyether ether ketones, ultrahigh molecular weight polyethylenes or polysulfones.

4. The intervertebral implant of claim 1, wherein the convex sliding portion and the concave sliding portion are made from a ceramic material.

5. The intervertebral implant of claim 1, wherein the upper apposition surface and the lower apposition surface have different shapes.

6. The intervertebral implant of claim 1, wherein the upper apposition surface and the lower apposition surface have the same shape.

7. The intervertebral implant of claim 1 wherein the upper apposition surface and the lower apposition surface are provided with macroscopic structures.

8. An intervertebral implant having a central axis comprising:
   an upper portion that comprises a first part having an upper apposition surface to contact a base plate of a vertebra lying above the upper apposition surface, and a separate second part having a concave sliding portion, the second separate part connectable to the first part and defining an interface extending therebetween;
   a lower portion that comprises a first part having a lower apposition surface to contact a cover plate of a vertebra lying below the lower apposition surface, and a separate second part having a convex sliding portion having an opening, the separate second part connectable to the first part and defining an interface therebetween, wherein the convex sliding portion and the concave sliding portion form a joint;
   a connecting element that comprises an anchoring element located on the same plane as the central axis, and a pin having a front end and a rear end, wherein the anchoring element further comprises a disk-shaped element connected to the front end of the pin, and the rear end of the pin extends through the separate second part of the upper portion and is fixedly connected to the first part of the upper portion, the pin extending through the opening of the separate second part of the lower portion so that the pin is moveable within the opening and does not interfere with the movement of the joint.

9. The intervertebral implant of claim 8, wherein the connecting element, during each articulation of the joint, permit an axial clearance of X>0 between the convex and concave sliding portions of the joint.

10. The intervertebral implant of claim 9, wherein the clearance X is at least 0.005 mm.

11. The intervertebral implant of claim 9, wherein the clearance X is at least 0.05 mm.

12. The intervertebral implant of claim 9, wherein the clearance X does not exceed 0.5 mm.

13. The intervertebral implant of claim 9, wherein the separate second part of the lower portion has a cavity, which is open at the apex of the convex sliding portion, and wherein the anchoring element can be moved axially so far that, after overcoming the clearance X, it comes to lie axially at the wall of the cavity.

14. The intervertebral implant of claim 8, wherein each component consists of an x-ray transparent material.

15. The intervertebral implant of claim 8, wherein the upper portion comprises a convex upper apposition surface and the lower portion comprises a convex lower apposition surface.

16. The intervertebral implant of claim 8, wherein the upper portion comprises an x-ray transparent material.

17. The intervertebral implant of claim 8, wherein the lower portion comprises an x-ray transparent material.

18. The intervertebral implant of claim 17, wherein the upper portion comprises the same x-ray transparent material as the lower portion.

19. The intervertebral implant of claim 8 wherein the first part of the upper portion includes a first x-ray transparent material and the second part of the upper portion includes a second x-ray transparent material.

20. The intervertebral implant of claim 8, wherein the first part of the upper portion includes a first x-ray transparent material and the second part of the upper portion includes a second x-ray transparent material, and the second part of the lower portion includes a second x-ray transparent material.

21. The intervertebral implant of claim 20, wherein the upper portion comprises a convex upper apposition surface and the lower portion comprises a convex lower apposition surface.

22. The intervertebral implant of claim 1, wherein the concave sliding portion is permanently connected with the upper portion and defines an interface extending therebetween.

23. The intervertebral implant of claim 22, wherein the convex sliding portion is permanently connected with the lower portion and defines an interface extending therebetween.

* * * * *